United States Patent
Refai

(10) Patent No.: US 8,157,832 B2
(45) Date of Patent: Apr. 17, 2012

(54) BLUNT DISSECTION AND TISSUE ELEVATION INSTRUMENT

(75) Inventor: Daniel Refai, St. Louis, MO (US)

(73) Assignee: Biospine, LLC, Columbia City, IN (US)

( * ) Notice: Subject to any disclaimer, the term of this patent is extended or adjusted under 35 U.S.C. 154(b) by 499 days.

(21) Appl. No.: 11/833,526

(22) Filed: Aug. 3, 2007

(65) Prior Publication Data

US 2008/0033474 A1 Feb. 7, 2008

Related U.S. Application Data

(63) Continuation-in-part of application No. 11/758,726, filed on Jun. 6, 2007, now abandoned.

(60) Provisional application No. 60/821,327, filed on Aug. 3, 2006.

(51) Int. Cl.
*A61B 17/00* (2006.01)

(52) U.S. Cl. ....................................... 606/190

(58) Field of Classification Search .................. 606/190, 606/192–198, 99, 207; 604/104, 174, 184
See application file for complete search history.

(56) References Cited

U.S. PATENT DOCUMENTS

| | | | |
|---|---|---|---|
| 4,477,256 A | | 10/1984 | Hirsch |
| 5,620,446 A | * | 4/1997 | McNamara et al. ............. 606/79 |
| 5,817,121 A | * | 10/1998 | Christoudias ................. 606/190 |
| 6,319,257 B1 | * | 11/2001 | Carignan et al. ................ 606/99 |
| 7,448,870 B2 | * | 11/2008 | Ma tre .......................... 433/114 |
| 2005/0230926 A1 | * | 10/2005 | Sakamaki et al. .............. 279/62 |

OTHER PUBLICATIONS

McKenna, Jr., et al., "Is lobectomy surgery by video-assisted thoracic surgery an adequate cancer operation?", The Annals of Thoracic Surgery, 1998.
Komanapalli, C., et al., "Thoracoscopic Management of Spontaneous Pneumothorax," CTSNet, Nov. 10, 2006.
Argote-Greene, L., et al., "Extrapleural Pneumonectory for Malignant Pleural Mesothelioma," MultiMedia Manual of Cardiothoracic Surgery, Jun. 28, 2005.
Mayo, Drawing, 1999.
Kitner Endoscopic Sponges, www.ivalon.net/catalog/endostik.htm.
Peanut Dissector Sponges, www.fabco.net/catalog/pnutdiss.htm.
Video depicting the posterior edge of the upper pleura held in a ring or tonsil clamp, and a peanut dissector used to develop an extrapleural plane (Nov. 10, 2006).
International Search Report and Written Opinion, PCT/US07/75183, dated Sep. 18, 2008.

\* cited by examiner

*Primary Examiner* — Victor Nguyen
(74) *Attorney, Agent, or Firm* — Heslin Rothenberg Farley & Mesiti P.C.

(57) ABSTRACT

A handheld medical instrument designed for efficient, atraumatic blunt tissue dissection and/or elevation during surgery. The instrument generally comprises an elongated shaft having a cottonoid or similar disposable dissection device at one or both ends. Attachment to the cottonoid may be direct or the shaft may include grasping constructs designed to grasp the cottonoid or to grasp a support structure which is attached to the dissection device. The devices may have reusable components or may be disposable.

21 Claims, 11 Drawing Sheets

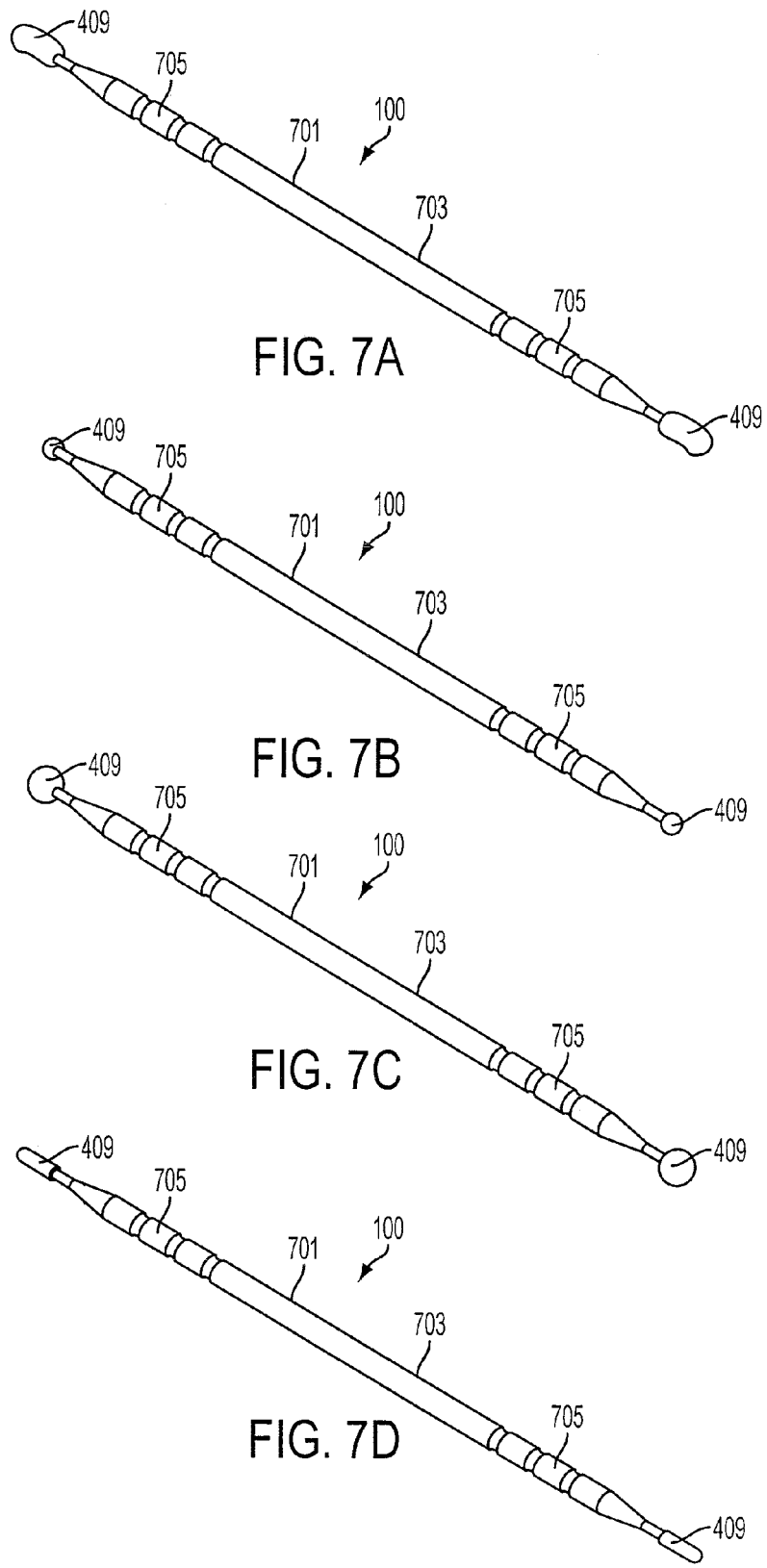

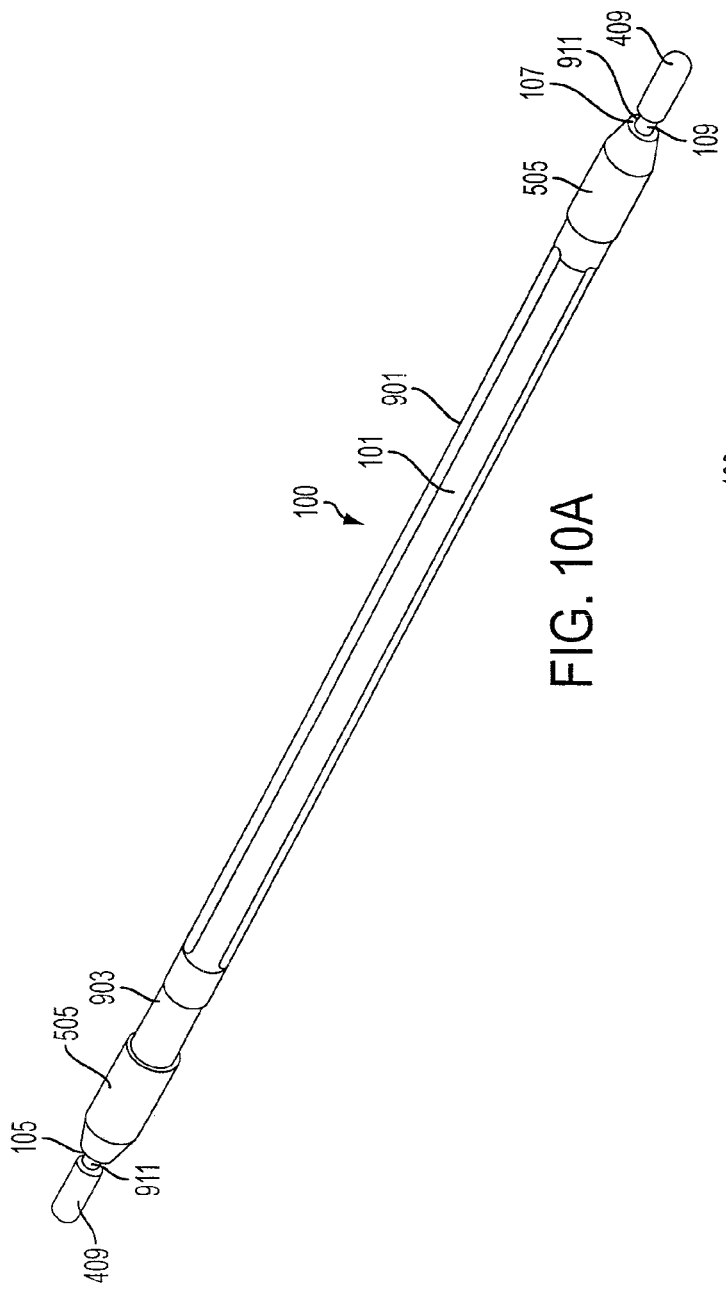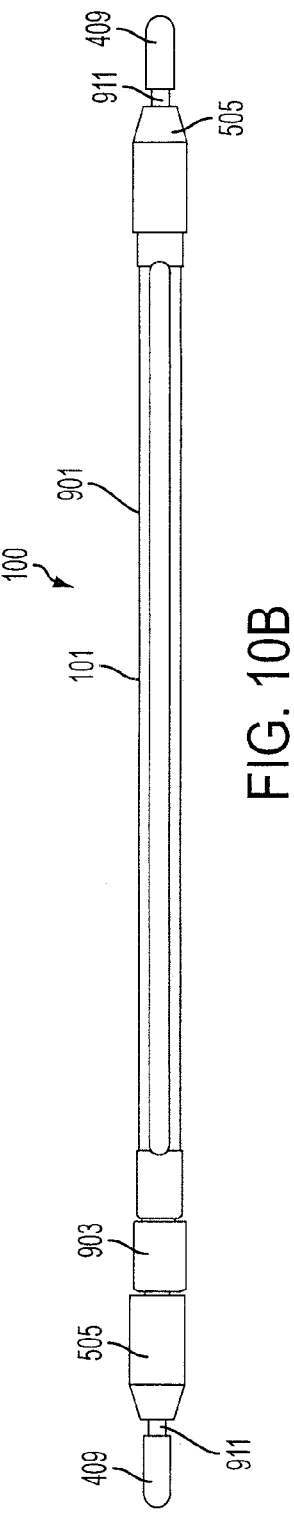

BLUNT DISSECTION AND TISSUE ELEVATION INSTRUMENT

CROSS REFERENCE TO RELATED APPLICATION(S)

This application is a Continuation-in-Part (CIP) of U.S. Utility patent application Ser. No. 11/758,726, filed Jun. 6, 2007 and now abandoned which in turn claims benefit of U.S. Provisional Patent Application Ser. No. 60/821,327 filed Aug. 3, 2006. This application further claims benefit of U.S. Provisional Patent Application Ser. No. 60/821,327 filed Aug. 3, 2006. The entire disclosure of all the above documents is herein incorporated by reference.

BACKGROUND

1. Field of the Invention

The present invention relates to a surgical device for use in blunt tissue elevation and/or dissection such as in cranial, spine, cervical, abdominal, thoracic, lumbar, endoscopic, laparoscopic, and other types of surgery.

2. Description of the Related Art

In many types of surgery it is necessary to remove or displace tissue in order to perform a procedure. Often, this is to improve a surgeon's vision in an area of interest where more delicate operations need to be performed, or may be to remove tissue which is in the way for a procedure as it either prevents the surgeon from accessing the area of interest with the tools they need to operate on it, or inhibits the application of a prosthetic or other surgical device. One of the more common types of surgery where removal of tissue is necessary is in implantation where it is often necessary to remove tissue from a bone so an artificial device, such as a support plate, can be attached. Removing the tissue provides for a stronger safer attachment and generally can result in an improved surgical outcome.

Depending on the nature of the tissue to be removed and its location, various different types of tools are desirable. The most common type of surgical removal tool is undoubtedly a sharp device such as a scalpel, blade, saw or drill. These types of devices are necessary for virtually any type of surgery to be performed as they allow the surgeon to cut through what would otherwise be a seamless body structure. In many situations, however, they are preferably not used as should the cutting instrument slip slightly, a very dangerous situation could occur. When a surgeon is working near essential blood vessels, organs, or other sensitive structures, the slightest misplacement or deviation of a sharp device can result in potentially traumatic injury or death.

The situation can be particularly dangerous if the surgeon is working on the spine or other central nervous system component. While an inadvertent cut to a blood vessel could create a potentially dangerous situation, blood vessels can often be repaired without lasting injury. A severed spinal cord, however, often cannot be repaired even with the most advanced procedures currently known. Because of these and other issues, it is therefore desirable that a surgeon use an instrument when working near the spinal cord or similar sensitive structures which, if it were to inadvertently contact nearby tissue, would have a decreased possibility of causing injury.

One such way to avoid this type of injury is to utilize a tool which is suitable for separating two types of matter along an existing seam or connection, but is generally unsuitable for "cutting" into seamless matter. This is often referred to as a blunt dissection instrument. Blunt dissection generally allows for tissues to be dissected atraumatically by simply separating the tissue along existing seams or natural planes. That is, the tool separates along natural separations, conjunctions, or faults, without the tool being able to create a new seam on its on. This type of instrument facilitates in surgical exposure and tissue retraction both because of reducing danger to neighboring tissue, and reducing trauma from manmade separation.

While blunt dissection is a useful medical practice, the tools for blunt dissection are generally ad-hoc and often ill-suited for the task. Current practice in blunt dissection generally involves using a makeshift device which is assembled in the operating room and provides the surgeon with a temporary support for holding a small blunt dissection pad having a relatively rough surface. Generally, this makeshift device consists of a traditional Kelly clamp (locking clamp) clamping a small blunt dissection pad commonly called a cottonoid, between its jaws. A "cottonoid" is a small, rolled piece of gauze commonly used in surgical procedures for a variety of activities. The cottonoid has a relatively rough surface which is capable of grasping tissue and supporting it to separate the tissue from adjoining tissue. This structure is generally unable to damage an intact organ, blood vessel, or similar structure as the cottonoid simply cannot grip tissue with sufficient force to separate structures without an existing seam, and is generally incapable of generating a new seam or separation on its own.

This makeshift device is unsuitable for the desired task of blunt dissection in many cases and can present dangers when used for such. In the first instance, the length of the Kelly clamp arm and handle necessarily limit the device to procedures relatively close to the location of the surgeon's hands. The structure of a clamp widens quite quickly to enable the clamp to be used for its principle purpose of clamping. The use of the device as a holders, therefore, is often relatively difficult and creates a less than ideal design. Further, sufficient depth of tissue dissection is often not possible with such a device and adequate exposure and visibility is therefore often difficult, if not impossible, because the device is held by the palm of the hand and lacks appropriate length and shape to perform the procedure.

Furthermore, a Kelly clamp is liable to become unlocked during a dissection and release the cottonoid into the patient, where it would need to be retrieved from a potentially sensitive area, as Kelly clamps are generally designed for relatively simple release. Finally, the Kelly clamp device is individually created by a surgical assistant and if the Kelly clamp is not loaded correctly with the cottonoid, or even if it is loaded differently than a surgeon was expecting, the metal tips of the Kelly clamp can come into unintentional contact with the surgical area. This contact can be adverse as the metal tips can act as a sharp dissection instrument when blunt dissection was intended, thus leading to unanticipated tissue injury and poor wound healing. This contact can also occur when the surgeon is least expecting it which can lead to an increased likelihood of injury.

To try and deal with some of the problems of a makeshift tool created from a Kelly clamp, disposable cottonoid devices designed principally for homeostasis are also sometimes used as endoscopic and laparoscopic dissectors. While they can resolve some of the concerns from the Kelly clamp device, these devices still have many of the same problems of the Kelly clamp improvised device such as a lack of sufficient length and a design intended for a different purpose. Further, these disposable cottonoid devices are often weak and can break or bend preventing them from being particularly useful in dissection as they are unable to provide sufficient separation force.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other reasons known to those of ordinary skill in the art, disclosed herein, among other things, is a handheld medical instrument designed for efficient, atraumatic blunt tissue dissection and/or elevation during surgery. This device generally provides for improved functionality and visibility over makeshift devices previously used for this task.

There is described herein, among other things, a surgical instrument, the instrument comprising a shaft, having two ends and a length therebetween; a chuck positioned at a first of the two ends of the shaft; a finger tightening mechanism capable of adjusting the chuck through rotation of the finger tightening mechanism; a support structure which is grasped by the chuck; and a blunt dissection pad attached to the support structure. That finger tightening mechanism can be rotated a first direction to open the chuck releasing the support structure from the chuck and the finger tightening mechanism can be rotated in a second direction to secure the support structure in the chuck.

In a further embodiment, the surgical instrument further comprises a second chuck, positioned at the second of the two ends; a second finger tightening mechanism capable of adjusting the second chuck through rotation of the second finger tightening mechanism; a second support structure which is grasped by the second chuck; and a second blunt dissection pad attached to the second support structure, wherein the second finger tightening mechanism can be rotated a first direction to open the second chuck releasing the second support structure from the second chuck and the second finger tightening mechanism can be rotated in a second direction to secure the second support structure in the second chuck.

In an embodiment, the shaft of the surgical instrument includes a textured portion along the length. In an embodiment, the instrument is made of metal. In an embodiment, at least a portion of the shaft includes a measurement marking.

In an embodiment, the blunt dissection pad comprises a cottonoid. In another embodiment, the blunt dissection pad is formed by winding fiber about a portion of the support structure.

In an embodiment, the shaft is separable into two portions at a point between the two ends to form a handle portion and a working end portion. In a further embodiment, that working end portion is intended for disposal after a single use. In another further embodiment, that handle portion is intended for disposal after a single use. In another further embodiment, that handle portion is intended for reuse. In another further embodiment, the working end portion is angled.

Also disclosed herein is a surgical instrument comprising a shaft formed as a single monolithic piece, having two ends and a length therebetween, the shaft comprising a central section connected to two textured sections, one of each of the textured sections being located toward each of the ends of the shaft and the central section located therebetween; two tapered sections, one of the tapered section connected to each of the textured sections; and two support structures, one of the support structures connected to each of the tapered sections; and two blunt dissection pads, one of the pads connected to each of the support structures in a fashion that is not intended to be removable.

In an embodiment of that surgical instrument, the pads comprise fibers wound about the support structures.

In another embodiment, the textured sections comprise grooves. In a further embodiment, each of the textured section includes three grooves.

In another embodiment, the shaft comprises a glass filled carbon rod. The shaft may also comprise plastic.

BRIEF DESCRIPTION OF THE DRAWINGS

FIG. 7 provides perspective views of four different embodiments of disposable blunt dissection instruments.

FIG. 10 provides multiple views of a multi-part blunt dissection instrument assembled with an straight working end.

DESCRIPTION OF THE PREFERRED EMBODIMENT(S)

Figure 1:
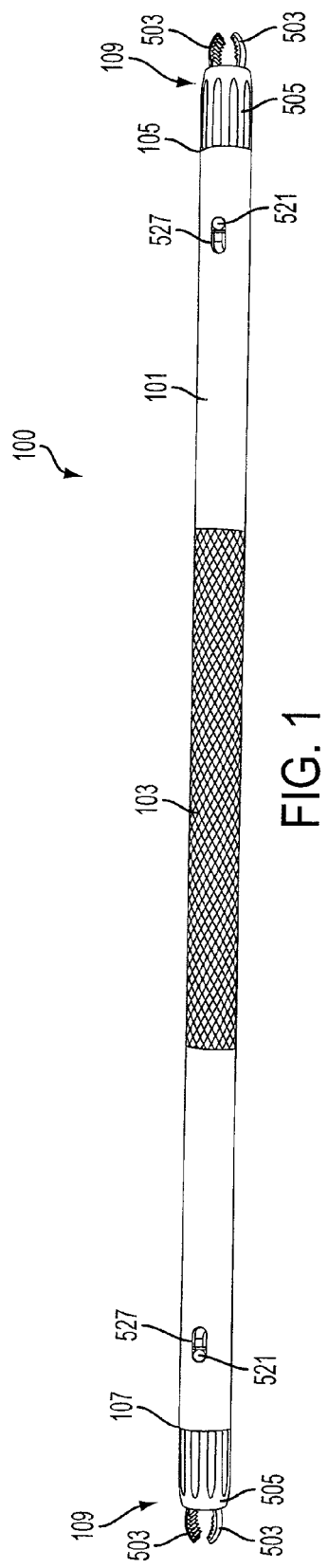
FIG. 1 is a side view of an embodiment of a blunt dissection instrument.

The following detailed description illustrates by way of example and not by way of limitation. Described herein, among other things, are embodiments of medical devices for use in blunt elevation and/or dissection of tissue. The devices are particularly of use in cranial or spinal surgery but the type of surgery for which it is used is in no way limited to such surgeries. The device will generally be referred to herein as a "blunt dissection instrument" or simply a "blunt dissector" or "dissector" for ease of discussion. This terminology is not intended to limit its use solely to dissection as the device may be used for a number of activities including, but not limited to, tissue elevation and blunt dissection.

FIGS. 1-4 provide for drawings of a first embodiment of a blunt dissection instrument (100). The remaining FIGS. provide for additional embodiments. The embodiments may be discussed simultaneously and interchangeably as many of their functional structures are similar and operate in a similar fashion. The blunt dissector (100) generally comprises an elongated shaft (101) with two ends (105) and (107). In the first depicted embodiment, the shaft (101) includes a grip section (103) which is knurled or otherwise textured and is located between the two ends (105) and (107) to provide for a comfortable surface for grasping by a human hand and an increase in friction between the blunt dissector (100) and the hand to improve manipulability and grip.

The blunt dissector (100), when used by a surgeon, is preferably held in the same general fashion as an individual holds a pencil. That is, the dissector (100) will generally be held between the thumb and opposing fingers at a point located on the grip section (103). This is as opposed to being held with the palm of the hand as the makeshift Kelly clamp device is generally held. This makes the blunt dissector (100) generally more convenient and comfortable for a surgeon to hold, provides for improved manipulability, and generally affords increased target tissue visibility and depth of tissue dissection. Further, the dissector (100) is generally more maneuverable as the fingers can manipulate it without need of additional support from the hand.

In the depicted embodiments of FIGS. 1 through 6 and 9 through 11, the blunt dissector (100) is constructed of metal, plastic, or other rigid and sturdy materials and is intended to be reusable. In an alternative embodiment depicted in FIGS. 7 and 8, the blunt dissector (100) is designed to be single use and disposable. The reusable embodiment will generally be sterilized in any manner known to those of ordinary skill in the art between patients and, consequently, will generally be more economical over time than disposable devices. Constructing the shaft (101) out of a rigid, reusable material such as metal also provides for increased strength to the blunt dissector (100) which will generally make the blunt dissector (100) more resistant to bending or breaking in the event the surgeon needs to apply pressure to the blunt dissector (100) in order to perform the desired procedure.

Figure 2:
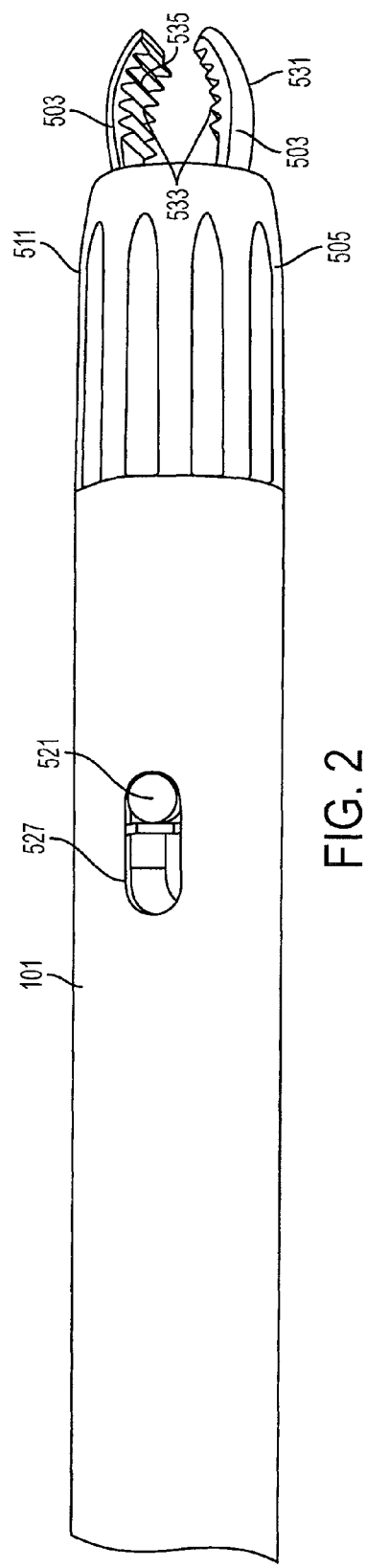
FIG. 2 is a side view of the embodiment of FIG. 1 showing detail of the jaws on one end of the instrument in the open position.
Figure 3:
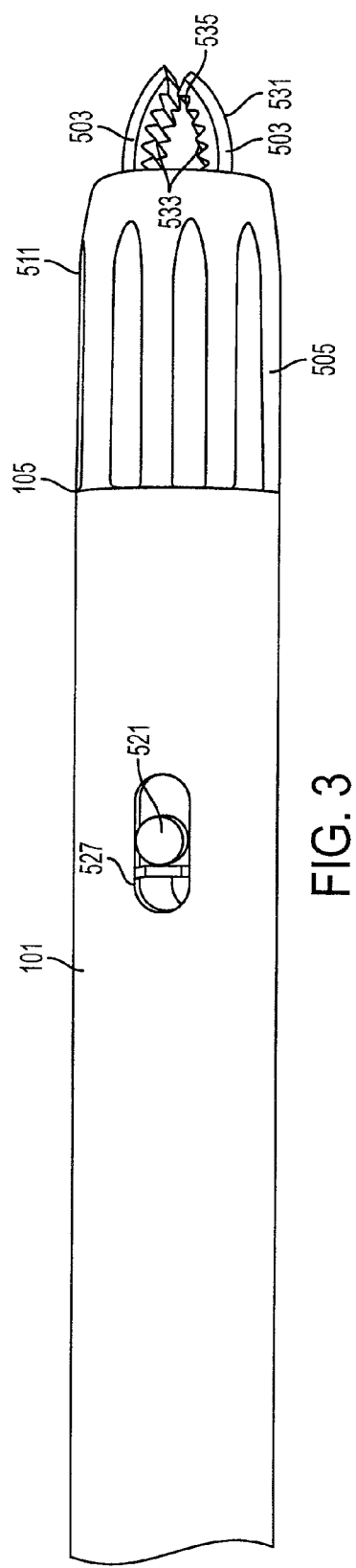
FIG. 3 is the side view of FIG. 2 showing the jaws in the closed position.
Figure 4:
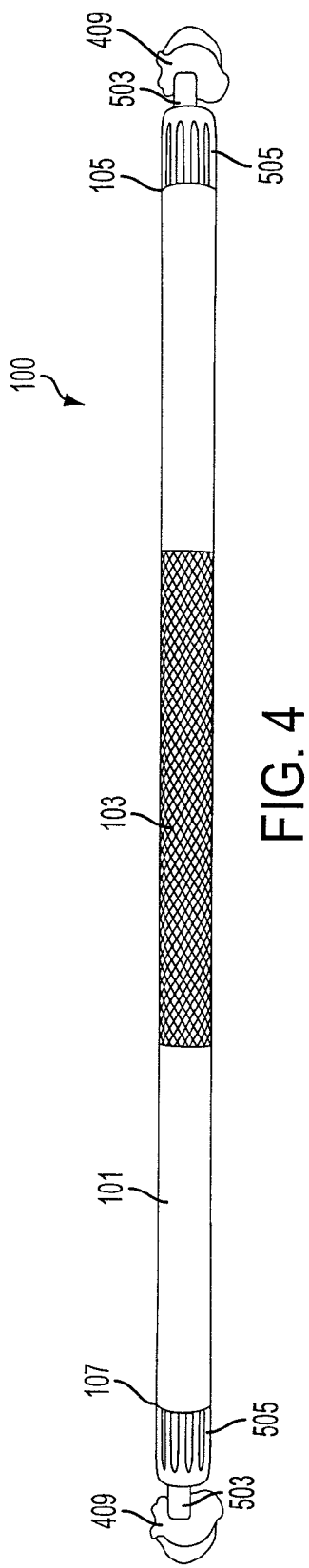
FIG. 4 is a top view of the embodiment of FIG. 1 showing the device grasping a cottonoid at each end.

In the depicted embodiments of FIGS. 1 through 6, at each of the two ends (105) and (107) there is provided a grasping construct (109). The grasping construct (109) serves to securely hold a blunt dissection pad (409) at each end of the shaft (101). The grasping construct (109) is generally sized and shaped to hold the blunt dissection pad (409) securely, while at the same time allowing the blunt dissection pad (409) to extend beyond the grasping construct (109) along the line of the shaft (101) in such manner that the structure of the grasping construct (109) is generally prevented from coming into contact with the tissue being dissected by the blunt dissection pad (409). Such a connection is shown in FIG. 4.

Figure 5:
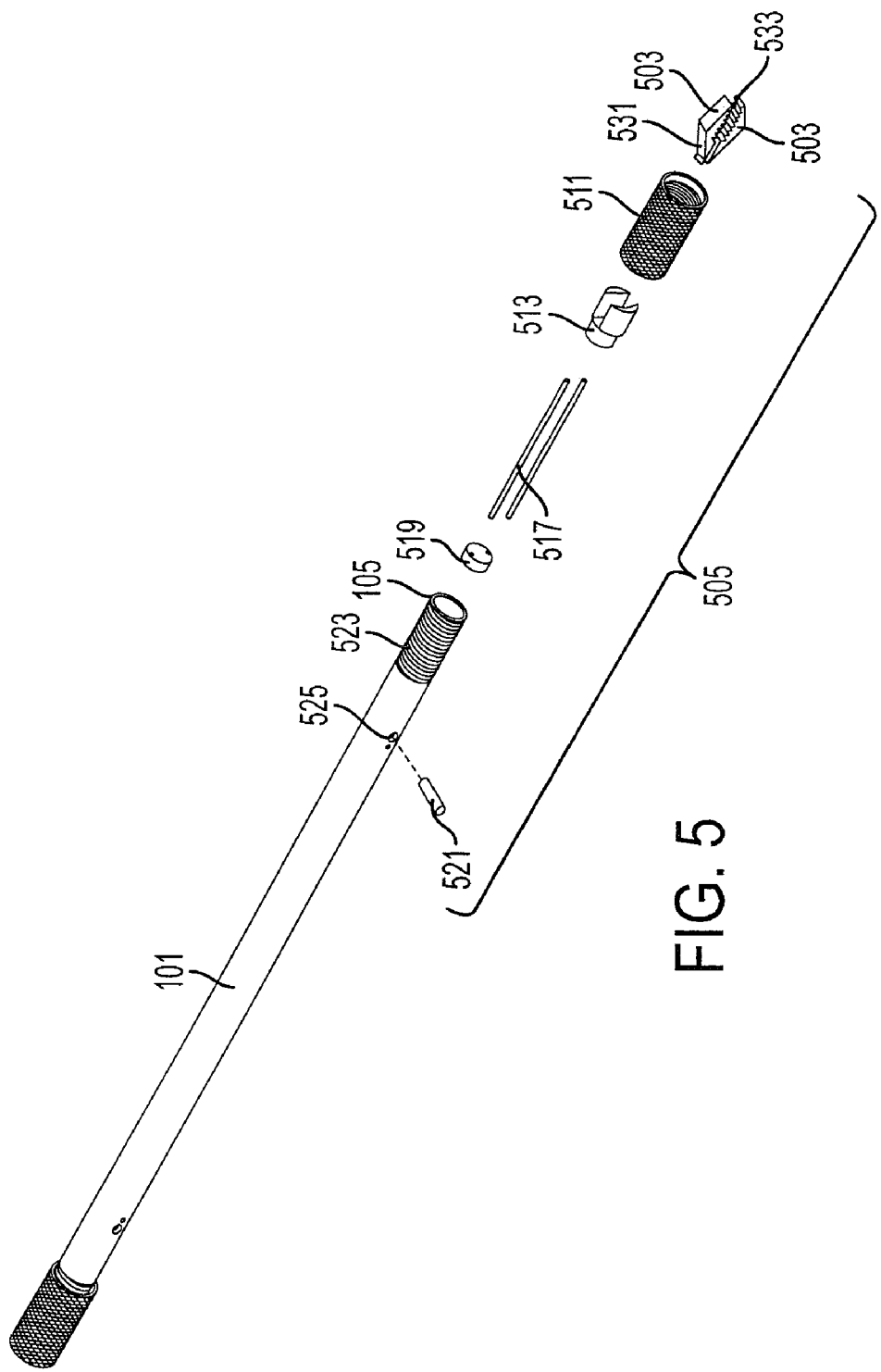
FIG. 5 is an exploded perspective view of another embodiment of a blunt dissection instrument.

In the depicted embodiments of FIGS. 1 through 6, each of the grasping constructs (109) comprises a pair of expandable jaws (503) which are capable of securely grasping blunt dissection pads (409) of varying sizes and types. The use of two jaws (503) is generally preferred, but by no means required, and in alternative embodiments, each grasping construct (109) will comprise three or more jaws (503). Further, one of ordinary skill in the art would recognize that the two jaws (503) need not necessarily be separate pieces, but may be attached together as shown in FIG. 5 while still functioning as separate jaws.

Generally, the blunt dissection pad (409) will comprise a cottonoid or similar small gauze or other textile structure having a relatively textured surface capable of being used to grasp tissue through friction. It is not necessary that the cottonoid be constructed of cotton or even textiles and devices constructed of substances such as, but not limited to, sponge, foam, or similar materials may be referred to as being cottonoids and blunt dissection pads (409). The jaws (503) will generally be designed to support one or more of the standard cottonoid sizes including, but not limited to, rosebuds, cherries, peanuts, Kittner's, and sponges.

In alternative embodiments, the blunt dissection pad (409) may comprise alternative structures to cottonoids such as, but not limited to, fibrous balls, wood pulp products, soft plastic products, or combinations of structures. In most embodiments, the blunt dissection pad (409) is only limited in that its structure is generally incapable of creating a seam in an otherwise intact structure in the human body. That is, it is not a knife, saw, or similar object designed to cut. Instead, the blunt dissection pad (409) provides a frictional surface capable of contacting tissue and separating it from adjacent tissue along an already existing (natural plane) transition line. Regardless of the construction or materials, the term "cottonoid" as used herein may be used to refer to the blunt dissection pad (409).

In the embodiments of FIGS. 1 through 6, the blunt dissector's (100) two sets of jaws (503) which are located on opposing ends of the blunt dissector (100) are preferably designed to operate independently of each other. That is, the jaws (503) at one end (105) of the shaft (101) may be opened or closed independently of the jaws (503) at the other end (107) of the shaft (101). Generally, the opening and closing of the jaws (503) will be accomplished by rotation of a finger tightening mechanism (505) which serves to open or close the jaws (503) depending on the direction of rotation. In the depicted embodiment, the opening or closing of the jaws (503) occurs as the jaws interact with the finger tightening mechanism (505) and/or the shaft (101) during the rotation. As should be apparent, the finger tightening mechanism is generally designed for manipulation by the fingers of a user.

The interaction is best explained by reference to FIG. 5. In the embodiment of FIG. 5, the finger tightening mechanism (505) from one end of the device is shown in exploded view. The finger tightening mechanism (505) includes a cuff (511) which is rotationally connected to the shaft (101), in this case, via a series of interacting screw threads (523). The jaws (503) are provided in a fashion that they are biased toward an open position. The jaws (503) (which in this depiction is a single construct) are fitted to a mount (513) which serves to hold the jaws (503) to the shaft (101). The mount is then connected by two rods (517) to a limiting plate (519). The limiting plate (519) is generally located within the shaft (101) and is connected to the shaft (101) via a pin (521) which extends through the shaft (101) via holes (525) in such manner as to prevent the limiting plate (519), and thus the jaws (503), from rotating.

In the finger tightening mechanism (505) shown in FIG. 5, the closing of the jaws (503) occurs because the cuff (511) can be extended from the end of the shaft (101) by being rotated about the screw threads, the rotation either moving the cuff toward or away from the shaft depending on the direction of rotation. As the cuff (511) extends from the end (105) of the shaft (101), the cuff (511) contacts the exterior surface (531) of the jaws (503). The exterior surfaces are angled in a manner such that contact from the cuff (511) serves to force the jaws (503) together as the cuff (511) extends from the shaft and over the jaws. The opposite movement of the cuff (511) allows the jaws (503) to open due to the biasing and effectively removal of the cuff's (511) blocking of the jaws' (503) opening. Generally, the jaws (503) will be shaped and sized so that at least a portion of the internal surfaces (533) of the jaws (503) are against each other or separated with very little space between them at a point along the allowed motion of the cuff (511). In this way, the jaws (503) can be closed on anything placed between them, regardless of its size.

Figure 6:
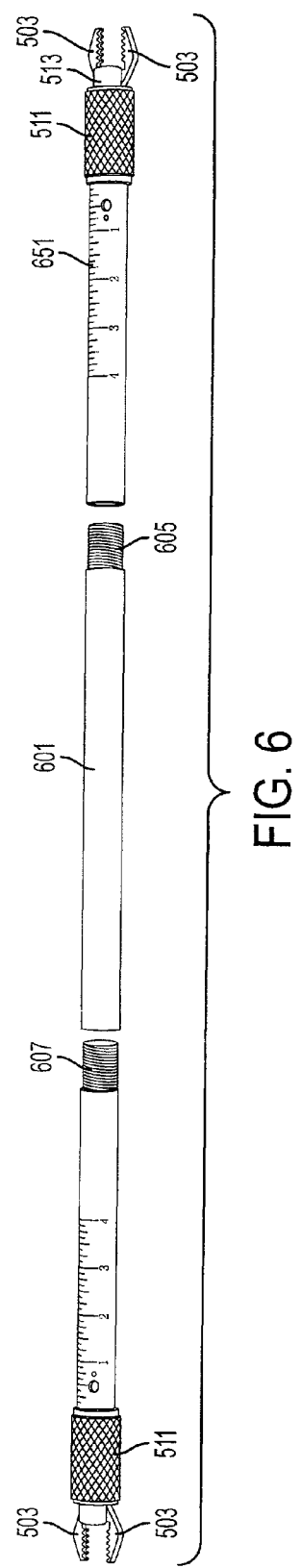
FIG. 6 is a side view of another embodiment of a blunt dissection instrument.
Figure 8A:
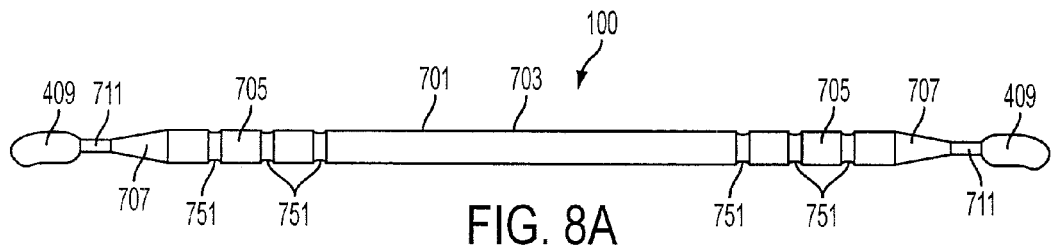
FIG. 8 provides side views of the embodiments of FIG. 7.
Figure 8B:
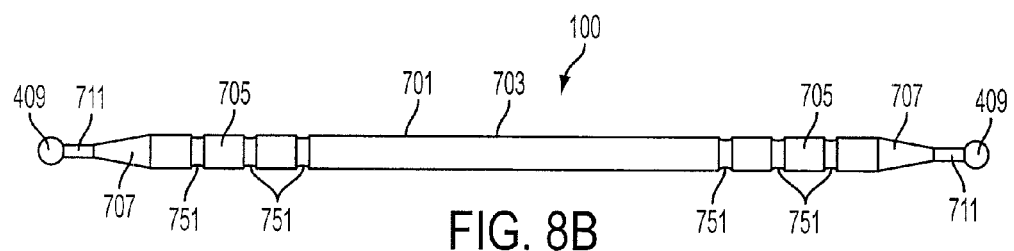
Figure 8C:
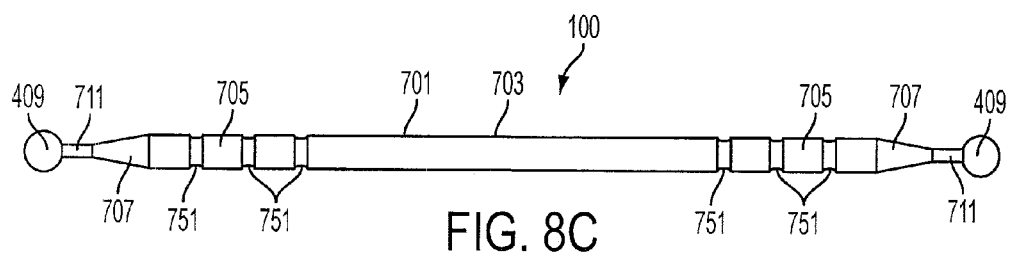
Figure 8D:
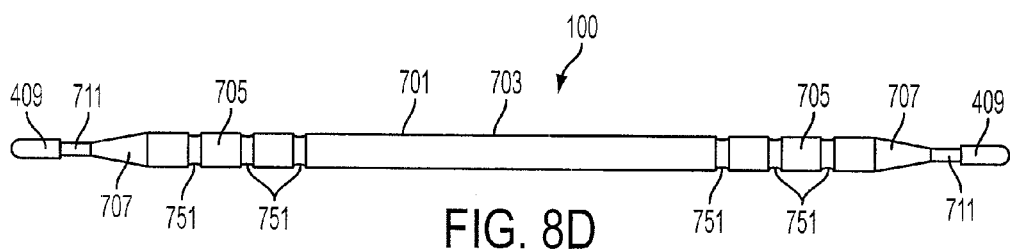

In the embodiments of FIGS. 5 and 6, the jaws (503) include a linearly angled exterior surface (531) and a generally linear interior surface (533). This can provide for an opening that is generally rectangular when the jaws (503) are open and is compressed into a generally "V" shape with the tip of the "V" being at the end of the jaws (503) when they are closed. This design is generally preferred as it provides for easier cottonoid insertion and improved grip strength, but is by no means required. In the embodiment of FIGS. 1-4, the jaws (503) are generally smoothly curving in both the exterior (531) and interior (533) surfaces which provides for a slightly different shape of closed jaws (503) as seen in FIG. 3. These jaw (503) shapes are simply two of many which may be used depending on construction methodology and desired grip style of the jaws (503).

While the embodiments of FIGS. 5 and 6 contemplate that the cuff (511) moves relative to the shaft (101) when the finger tightening (505) is activated, the embodiment of FIGS. 1-4 provides for an alternative methodology. In this embodiment, the cuff (511) is allowed to freely rotate about the end (105) of the shaft (101), instead of extending or retracting on threads. In this embodiment, the mount (513), or similar structure, is deigned to move on threads or similar structures moving the jaws (503) interior to the cuff (511) toward and away from the end (105) or (107) of the shaft (101). In this case, the pin (521) will generally be placed into an elliptical runway hole (527) (as best shown in FIGS. 2 and 3) and will be able to move along a portion of the length of the shaft (101). In this situation, the closing of the jaws (503) may serve to limit the extent of retraction of the jaws (503), or the pin's (521) freedom of movement may prevent the jaws (503) from opening or closing more than is desired. The movement of the pin (521) is shown between FIGS. 2 and 3 which show the jaws (503) in open and closed positions respectively.

The opening and closing of the jaws (503) need not be performed through such a screwable rotation as described in the above embodiments. However, it is preferred that the opening and closing of the jaws (503) be performed through a process which requires relatively significant movement of the operator so that the jaws (503) are not inadvertently released or connected. A more motion intensive mechanism requiring increased movement to release is preferred as it provides for generally more secure grasping of the cottonoid (409) and reduces the risk that the jaws (503) could separate or unlock inadvertently during use of the blunt dissector (100). This helps to inhibit the possibility of the cottonoid (409) separating from the blunt dissector (100) in use and then having to be retrieved from the patient.

Due to the size and positioning of the jaws (503), the jaws (503) are either forced together or allowed to spread apart depending on the direction the finger tightening mechanism (505) is rotated. This variable size opening of jaws (503) allows the jaws (503) to accommodate a variety of different sized cottonoids (409) and allows each to be securely clamped to the blunt dissector (100).

The jaws (503) preferably include a plurality of internal teeth (535) or a similar high friction surface which can be used to securely grasp a blunt dissection pad (409) which is placed between the jaws (503) and inhibit the blunt dissection pad (409) from being pulled from within the closed jaws (503) during the procedure. It is preferred that a significant force be required to pull the blunt dissection pad (409) from within the jaws (503) and that, in an embodiment, the force required to remove the blunt dissection pad (409) from the jaws (503) is greater than the force to disassociate parts of the blunt dissection pad (409) from each other.

In the embodiments of FIGS. 1 through 6, there is a grasping construct (503) and associated finger tightening mechanism (505) at each end of the shaft (101). This structure is generally preferred but is not required and in alternative embodiments a grasping construct is only placed on a single end. The two-ended structure allows for a cottonoid (409) to be placed on each end of the blunt dissector (100) simultaneously. By having a grasping construct (109) on both ends of the blunt dissector (100), two different sizes, textures, or other propertied blunt dissection pads (409) can be used interchangeably without need to switch instruments (100). This gives the surgeon a more versatile tool that is both bi-directional and potentially bi-functional. It also generally eliminates the need to switch between instruments when the surgeon needs a larger or smaller dissection pad (409). Still further, even if two different sizes of dissection pads (409) are unnecessary, it gives the surgeon two readily available blunt dissection pads (409) allowing a switch if one was to become full of tissue, damaged, or for some other reason was unsuitable.

To meet the specific needs of different types of procedures (cranial, thoracic, abdominal, etc.), the shaft (101) may be designed in various diameters and lengths. In one embodiment, the depicted blunt dissector (100) would be provided as one of a series of blunt dissectors (100) provided as a set. Such a set may include a number of different blunt dissectors (100) having different lengths and/or diameters. A larger diameter dissector (100) may be needed on a procedure where greater force is required for the dissection, when a larger dissection pad (409) is desired, or there is greater access to the area of interest. Conversely, a smaller diameter blunt dissector (100) might be necessary to afford access to a smaller location or to provide a wider field of view around the blunt dissector (100). A smaller diameter blunt dissector (100) may also be necessary in situations where smaller incisions are preferred or when working on more delicate areas where neighboring structures can be more readily injured. Likewise to the diameter, the shaft (101) may be designed to different lengths. A longer length shaft (101) would generally be more desirable when accessing deeper areas, while a shorter shaft (101) will generally be more convenient and provide for greater control if the depth of the procedure is less.

In an embodiment there is provided a kit of dissectors, the kit would be provided including a number of different blunt dissectors (100). Depending on the type of surgical operation the kit is designed for, the blunt dissectors (100) may specifically be chosen and provided based on increased need in these types of procedures. The kit may also include repeated sizes if the procedure may require significant dissection quickly to allow for the surgeon to be using one tool while an assistant is swapping out or loading a new dissection pad (409) on another.

In a still further embodiment, the shaft (101) may be modified to be two or more separable pieces such as is shown in FIGS. 6 and 9-11. In particular, at a point between the two ends (105) and (107) the shaft (101) may be separable into two pieces, such as, for instance, by unscrewing them. In the embodiment of FIG. 6, variable lengths of shafts (101) could be obtained for the blunt dissector (100) by providing screw-in extension shafts (601) which interact with screw threads (605) and (607) on each end and are designed to be screwed between the two end pieces of shaft (101). A variety of such shaft extensions (601) could be provided with each blunt dissector (100) If a shorter blunt dissector (100) was desired, the user could use a short extension or simply screw the two end pieces together. If an even shorter device was required, one end could be used alone. To provide a longer device, a longer extension (601) could be used.

Figures 9A, 9B:
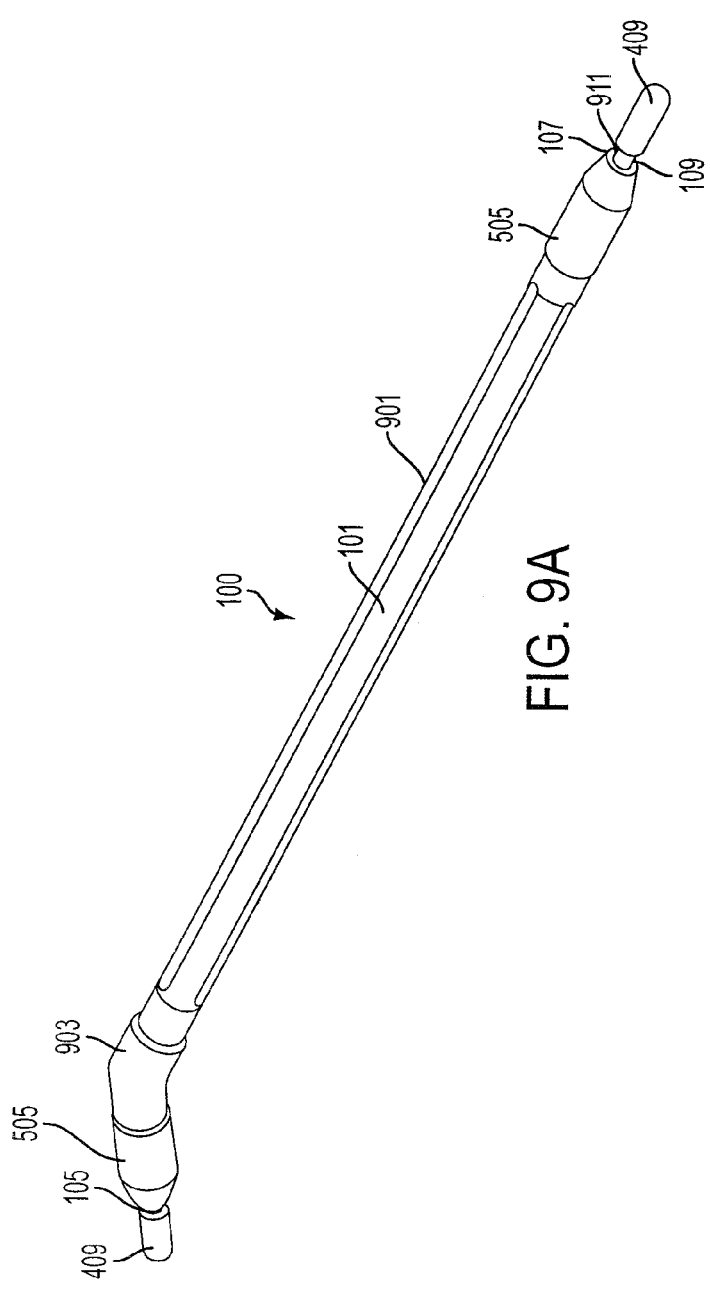
FIG. 9 provides multiple views of a multi-part blunt dissection instrument assembled with an angular working end.
Figure 11A:
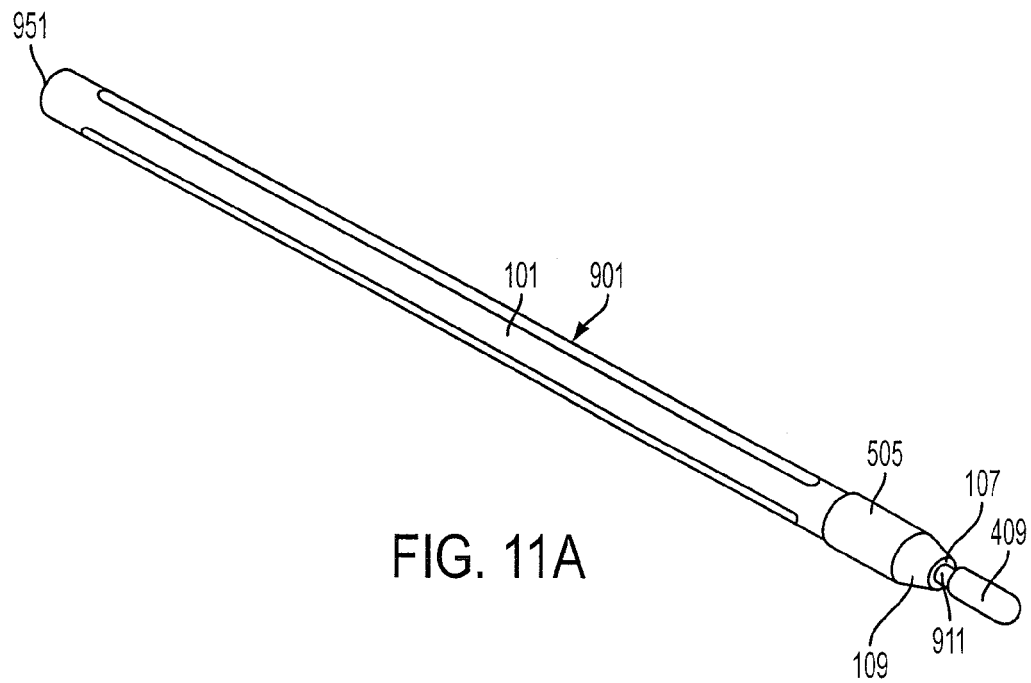
FIG. 11 provides views of the handle portion and two working end portions which may be attached thereto to form the instruments of FIGS. 9 and 10.
Figure 11B:
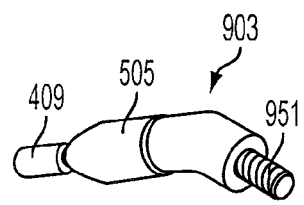
Figure 11C:
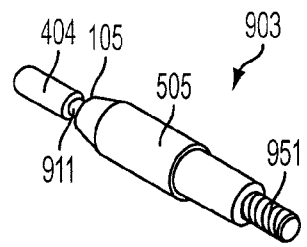

As shown in FIGS. 9-11, the shaft (101) may be made up of a handle portion (901) which comprises the majority of the shaft (101) and a working end (903) which may comprise one of a number of different shapes. The embodiment shown in FIGS. 9-11 also show an alternative form of connection to the cottonoid. In the embodiment of FIGS. 9-11, the handle portion (901) is designed to only have one working end (903) which is removable at a single end of the shaft (101). This is by no means necessary and working ends could be attached at one or both ends of the shaft (107). As discussed previously, the working portion (903) and handle portion (901) may include interlocking connectors such as mating screw threads (951) for interconnection.

As shown in FIG. 9, the working end (903) may be selected to provide for an angle or other arrangement which adjusts the position of the cottonoid so that it is not necessarily collinear with the shaft (101). Instead, the cottonoid may be provided at an angle to the handle portion (901) so as to allow working in areas which may be difficult to access directly. In an alternative embodiment, the angle at which the blunt dissection pad (409) is held relative to the handle portion (901) may be adjustable via a joint structure such as a locking joint of type known to those of ordinary skill in the art, so that the user can adjust the angle to a desired value and maintain it at that angle during use.

The working end (903) may be intended to be reusable and may grasp the cottonoid as contemplated above in the embodiments of FIGS. 1 through 6. In the embodiment of FIGS. 9 through 11, however, the grasping construct (109) is designed to grasp in a different fashion. In the embodiment of FIGS. 9-11, the grasping construct (109) does not grasp the blunt dissection pad (409) directly, but instead grasps a support structure (911) holding the blunt dissection pad (409). In one embodiment, the blunt dissection pad (409) comprises fibers wrapped around and generally permanently attached to the support structure (911). The support structure (911) may be composed of any material but in an embodiment will be plastic or other relatively soft material. The support structure (911) will also generally be shaped so as to not include sharp edges. The support structure (911) extends beyond a portion of the blunt dissection pad (409) so as to provide for a grasping surface. This surface is then grasped by the grasping construct (109). Instead of having the large grasping jaws as contemplated in FIGS. 1-6, the embodiment of FIG. 9 generally uses an internal chuck to grasp the extended end of the support structure (911). This chuck will generally be a self-centering or universal chuck sized and shaped to grasp the support structure (911). In effect, this connection may operate in the same fashion as a traditional chuck in a pin-vise or drill. Adjustment of the chuck may again be accomplished by manipulation of the finger tightening mechanism (505) to open or close the chuck in similar fashion to the opening and closing of the jaws (503) of the embodiments of FIGS. 1-6.

In a still further embodiment, the blunt dissection pad (409) may be formed about the support structure (911) which is then permanently attached to the working end portion (903). The working end portion (907) may then be entirely disposable after use with the handle portion (901) being either also disposable (which simply allows the user to select the combination of components they want for each particular surgery) or the handle portion (901) may be reusable with a number of disposable working portions (903).

As shown in FIG. 6, a ruler (651) or other measurement marking may be placed on the shaft (101) so that tissue depth can be measured from each end. This can enable the surgeon to quickly and efficiently determine the size of retractor blades or other devices needed in subsequent steps of the surgery and to determine the depth at which the instrument (100) is being used if vision is uncertain.

While the embodiment of FIGS. 1-6 and 9-11 are generally intended to allow for replacement of blunt dissection pads (409) as necessary (such as between procedures) with at least a portion of the shaft (101) being reused, it is not required that the shaft (101) or any portion of the instrument (100) be reusable. In the embodiments of FIG. 7-8, the instrument (100) is intended to be disposed of after a single use. In these embodiments, the shaft (701) is formed as generally a single monolithic piece and will comprise a central section (703), tapered sections (707), and the supporting structure (711) for the blunt dissection pad (409). The central section (703) will often be smoother and serve to provide the structure with its length. In the depicted embodiments, a textured section (705) is attached on each end of the central section (703) toward each end of the shaft (701). This textured section (705) may include texturing as contemplated in the embodiments of FIGS. 1-6, or may, as shown in FIG. 8 provide for simply a series of troughs (751) in the surface to improve grip. These troughs (751) can provide for a gripping surface to inhibit the user's hands from moving relative to the shaft (101) when the instrument (100) is in use.

From the textured sections (705) the shaft (701) will generally have a tapered section (707) at each end where the shaft (101) tapers to a smaller cross-sectional area and forms a support structure (711) for the blunt dissection pad (409). This support structure (711) will generally be similar to the support structure (911) and again the blunt dissection pad (409) will be attached directly to the support structure (711) in a generally permanent fashion. As a blunt dissection pad (409) often comprises a ball of wound thread, in an embodiment the blunt dissection pad (409) will comprise fibers wound directly on the support structure (711) and possibly further secured with an adhesive.

As shown in FIGS. 7 and 8, the disposable instrument (100) may be formed with a variety of differently shaped blunt dissection pads (409) including peanuts, rosebuds, cherries, or Kittners. While in the depicted embodiments, both pads (409) have the same shape, the device (100) may be formed with ends having different shapes from each other.

The disposable devices (100) of FIGS. 7 and 8 can provide for certain benefits. In an embodiment, the device (100) can be significantly less expensive to construct with the shaft being made of plastic (generally a relatively soft plastic), carbon fiber, glass filed carbon rod, or other similarly lightweight materials which are still sufficiently rigid to impart strength. It is preferable that the materials be sufficiently rigid that the shaft not bend until a significant amount of force is applied and generally non-porous so that the shaft (701) does not soak up body fluids and weaken, but those characteristics are by no means required.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A surgical instrument comprising:
a shaft having a first end and a second end and a length therebetween;
a first coupling mechanism positioned at the first end of said shaft and a second coupling mechanism positioned at the second end of said shaft;
at least one blunt dissector pad support structure configured to be coupled by at least one of said first coupling mechanism and said second coupling mechanism; and
at least one blunt dissector pad attached to a distal portion of said at least one blunt dissector pad support structure.

2. The instrument of claim 1,
wherein the first coupling mechanism is connected to the first end of the shaft and the second coupling mechanism is connected to the second end of the shaft.

3. The instrument of claim 2, wherein an axis of the at least one blunt dissector pad support structure is angled relative to an axis of elongation of the shaft.

4. The instrument of claim 2, wherein an axis of the at least one blunt dissector pad support structure is collinear to an axis of elongation of the shaft.

5. The instrument of claim 1, wherein said shaft includes a textured portion along said length.

6. The instrument of claim 1, wherein said blunt dissector pad comprises a cottonoid.

7. The instrument of claim 1, wherein said blunt dissector pad comprises wound fibers.

8. The instrument of claim 7, wherein said at least one blunt dissector pad support structure is disposable after a single use.

9. The instrument of claim 7, wherein said at least one blunt dissector pad support structure is reusable.

10. The instrument of claim 1, wherein said shaft is made of metal.

11. The instrument of claim 1, wherein at least a portion of said shaft includes a measurement marking.

12. The instrument of claim 1, wherein the first coupling mechanism and the second coupling mechanism are rotatable chucks.

13. The instrument of claim 1, wherein the first coupling mechanism and the second coupling mechanism each comprise a set of internal threads, the set of internal threads configured to threadingly engage a set of external threads positioned at a proximal end of the at least one blunt dissector pad support structure.

14. The instrument of claim 1, wherein the at least one blunt dissector pad is fabricated from at least one of a fibrous ball, a wood pulp-material, and a plastic material.

15. The instrument of claim 1, wherein the at least one blunt dissector pad support structure comprises a first blunt dissector pad support structure and a second blunt dissector pad support structure, and wherein the first blunt pad dissector support structure is coupled to said first coupling mechanism and the second blunt dissector pad support structure is coupled to said second coupling mechanism.

16. The instrument of claim 15, wherein the at least one blunt dissector pad comprises a first blunt dissector pad and a second blunt dissector pad, and wherein the first blunt dissector pad is attached to the distal portion of the first blunt dissector support pad structure and the second blunt dissector pad is attached to the distal portion of the second blunt dissector pad support structure.

17. A surgical instrument comprising:
a monolithic shaft having two ends, said shaft further comprising:
a central section integrally connected to two textured sections, each of said textured sections located toward each of said two ends of said shaft and said central section located therebetween; and
two tapered sections, each tapered section integrally connected to one of said two textured sections;
two blunt dissector pad support structures, each of said two blunt dissector pad support structures integrally connected to one of said two tapered sections; and
two blunt dissector pads, one of said two blunt dissector pads attached to a first of said two blunt dissector pad support structures and another of said two blunt dissector pads attached to a second of said two blunt dissector pad support structures.

18. The instrument of claim 17, wherein each of said two textured sections comprise at least one circumferential groove.

19. The instrument of claim 17, wherein said monolithic shaft is fabricated from a glass filled carbon material.

20. The instrument of claim 17, wherein said monolithic shaft is fabricated from plastic.

21. The instrument of claim 17, wherein the two blunt dissector pads are fabricated from at least one of a fibrous ball, a wood-pulp material, and a plastic material.

* * * * *